(12) United States Patent
Tai et al.

(10) Patent No.: US 8,845,979 B2
(45) Date of Patent: Sep. 30, 2014

(54) THERMAL BLOOD CLOT FORMATION AND USE IN MICROFLUIDIC DEVICE VALVING APPLICATIONS

(75) Inventors: Yu-Chong Tai, Pasadena, CA (US); Wendian Shi, Pasadena, CA (US); Luke Guo, San Diego, CA (US)

(73) Assignee: California Institute of Technology, Padasena, CA (US)

( * ) Notice: Subject to any disclaimer, the term of this patent is extended or adjusted under 35 U.S.C. 154(b) by 590 days.

(21) Appl. No.: 13/232,776

(22) Filed: Sep. 14, 2011

(65) Prior Publication Data

US 2012/0064552 A1 Mar. 15, 2012

Related U.S. Application Data

(60) Provisional application No. 61/382,867, filed on Sep. 14, 2010.

(51) Int. Cl.

| | | |
|---|---|---|
| *G01N 33/49* | (2006.01) | |
| *F16K 99/00* | (2006.01) | |
| *B01L 3/00* | (2006.01) | |
| *G01N 33/86* | (2006.01) | |
| *G01N 35/00* | (2006.01) | |

(52) U.S. Cl.
CPC ......... *G01N 33/86* (2013.01); *B01L 2400/0406* (2013.01); *B01L 2400/0677* (2013.01); *B01L 2400/0442* (2013.01); *G01N 2035/00247* (2013.01); *B01L 3/502738* (2013.01); *F16K 99/004* (2013.01); *F16K 2099/0084* (2013.01); *B01L 3/5027* (2013.01); *B01L 2300/1827* (2013.01); *B01L 2300/1861* (2013.01); *F16K 99/0032* (2013.01); *B01K 3/502707* (2013.01); *G01N 33/49* (2013.01); *B01L 2300/0816* (2013.01)

USPC .................. 422/502; 137/13; 422/507; 435/4; 435/13

(58) Field of Classification Search
CPC .................. B01L 3/502738; B01L 2400/0442; B01L 3/5027; B01L 3/502707; B01L 2400/0677; F16K 99/0032; F16K 99/004; F16K 2099/0084; G01N 2035/00247; G01N 33/49

See application file for complete search history.

(56) References Cited

U.S. PATENT DOCUMENTS

| | | |
|---|---|---|
| 4,074,719 A | 2/1978 | Semm |
| 2003/0012657 A1 | 1/2003 | Marr et al. |
| 2004/0147032 A1 * | 7/2004 | Martin et al. .................. 436/69 |
| 2007/0227592 A1 | 10/2007 | Allen |
| 2008/0058192 A1 | 3/2008 | Cho |
| 2008/0255639 A1 * | 10/2008 | Stumpp et al. .................. 607/89 |
| 2008/0294029 A1 * | 11/2008 | Piveteau et al. ............... 600/369 |
| 2009/0104637 A1 | 4/2009 | Ismagilov et al. |

OTHER PUBLICATIONS

International Search Report and Written Opinion for International Application No. PCT/US2011/051615 mailed Apr. 24, 2012.
Glass, "The Thermal Coagulation Point of Blood Serum," *The American Journal of Medicine*, vol. 8, Issue 6, pp. 745-754 (Jun. 1950).

\* cited by examiner

*Primary Examiner* — Jon P Weber
*Assistant Examiner* — Charles Zoltan Constantine
(74) *Attorney, Agent, or Firm* — Kilpatrick Townsend & Stockton LLP

(57) ABSTRACT

The present invention provides a method of forming a blood-clot microvalve by heating blood in a capillary tube of a microfluidic device. Also described are methods of modulating liquid flow in a capillary tube by forming and removing a blood-clot microvalve.

20 Claims, 4 Drawing Sheets

THERMAL BLOOD CLOT FORMATION AND USE IN MICROFLUIDIC DEVICE VALVING APPLICATIONS

CROSS-REFERENCES TO RELATED APPLICATIONS

This application claims priority to U.S. Provisional Applictaion No. 61/382,867, filed Sep. 14, 2010.

STATEMENT AS TO RIGHTS TO INVENTIONS MADE UNDER FEDERALLY SPONSORED RESEARCH AND DEVELOPMENT

The invention described herein was made in the performance of work under a NASA contract NCC 9-58, subcontract TD01301, and is subject to the provisions of Public Law 96-517 (35 USC 202) in which the Contractor has elected to retain title.

BACKGROUND OF THE INVENTION

Microfluidic technology has been studied extensively to develop low-cost lab-on-a-chip devices. These devices often require the use of simple, reliable valves to facilitate their operations. Many MEMS-based valving principles, such as utilizing magnetostatics, electrostatics, pneumatics or thermal actuation of movable membranes, have been thoroughly studied, but the fabrication and/or the operation of these valves could still be complicated. Therefore, valves with simple structure such as those operated by using phase-change materials or rheological materials are of great interest.

Unfortunately, there is still a lack of simple microvalves especially for on-chip blood analysis. Interestingly, blood is a fluid that can coagulate under the right conditions, and this coagulation process may provide a natural valving mechanism that has not been well explored in microfluidics. In blood vessels, solid blood coagulum can be formed through biological clotting process to stop bleeding. Similarly, others methods can be used to trigger the blood coagulation. For example, thermal coagulation uses heating to introduce the blood clogging, which is mainly a process of protein denaturation and cross linking. This coagulation property of blood provides an interesting alternative to traditional valving mechanisms. A valve using blood coagulation as the actuation method needs no extra material other than the blood sample itself, which is readily available in devices targeting for blood analysis. Surprisingly, the present invention meets this and other needs.

BRIEF SUMMARY OF THE INVENTION

In one embodiment, the present invention provides a method of forming a blood-clot microvalve in a capillary tube or microchannel of a microfluidic device. The method includes heating blood in the capillary tube or microchannel at a temperature of from about 50° C. to about 100° C. for a sufficient period of time, such that a solid blood coagulum is formed having a threshold differential pressure of from about 0 psi to about 100 psi. Thus, the method forms the blood-clot microvalve.

In other embodiments, the present invention provide a method of modulating liquid flow through a capillary tube or microchannel of a microfluidic device. The method includes heating blood in the capillary tube or microchannel at a temperature of from about 50° C. to about 100° C. for a sufficient period of time, such that a solid blood coagulum is formed having a threshold differential pressure of from about 0 psi to about 100 psi, thus modulating the liquid flow through the capillary tube.

clog sizes, including results from both capillary tubes and PDMS devices. Same heating condition (80° C., 30 min) was used for the clogging. For the results from PDMS devices, the pressure of 50 psig or higher means the PDMS delaminated from the glass substrate before the clog failing the test.

Figure 7:
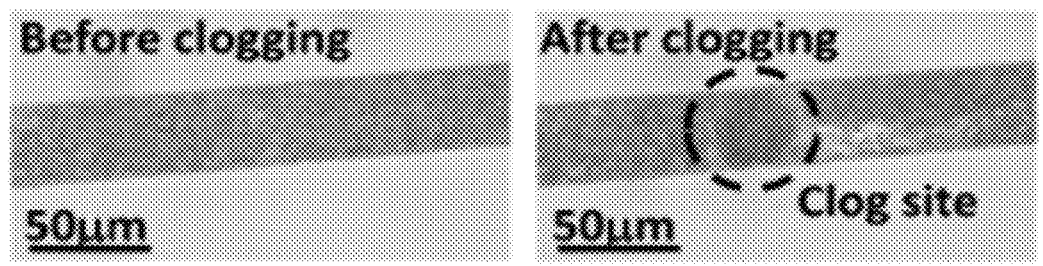

FIG. 7 shows microscopy pictures of the blood in a PDMS channel before (Left) and after (Right) laser-induced clogging. The outline of the clog site is defined by the size of the laser spot (40 μm diameter), which is slightly wider than the fluidic channel (36 μm wide).

Figure 8:
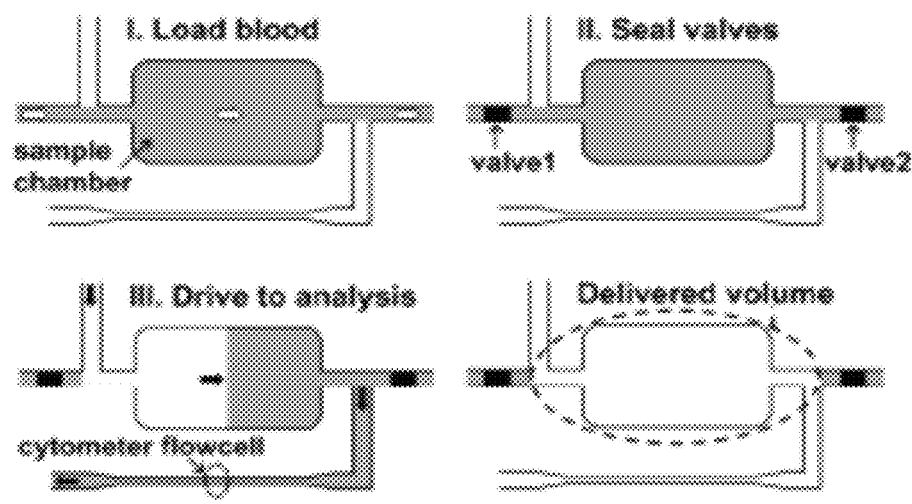

FIG. 8 shows an illustration of implementing the laser-induced clogging valve for sample volume control in a microfluidic cytometer. The sample chamber has four fluidic ports. The top port connects to an upstream pump. The bottom port connects to a narrowed channel, which serves as a cytometer flowcell. The left and right channels are blood loading ports as well as the sites of the clogging valve.

Figure 9:
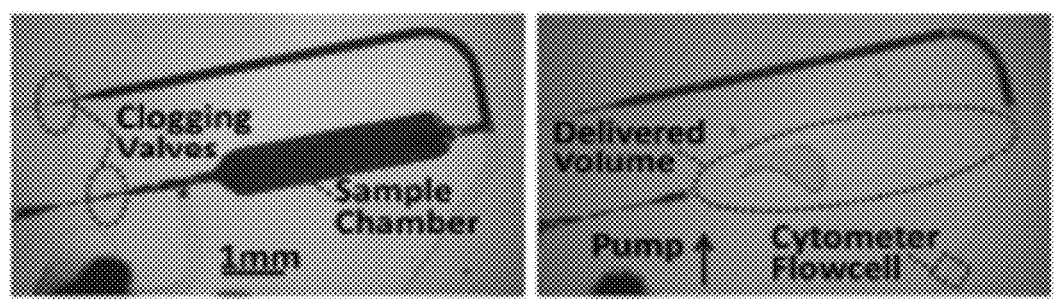

FIG. 9 shows microscopy pictures of the PDMS device and the operation of implementing the laser-induced clogging valve in a microfluidic cytometer. (Left) Blood was loaded into the sample chamber and sealed inside by two clogging valves. (Right) The sample was pushed out by a syringe pump for downstream analysis in a cytometer flowcell.

DETAILED DESCRIPTION OF THE INVENTION

I. General

The invention is a method of forming a microvalve in a capillary tube of a microfluidic device, where the microvalve is prepared from blood by heating the blood at a sufficiently high temperature to form a solid blood coagulum that blocks the flow of blood in the capillary tube. The heating can be localized to one segment of the capillary tube, or can be to the entire microfluidic device.

Without being bound to any one theory, blood thermal coagulation is a complex phenomenon that encompasses several processes including deformation and rupture of erythrocytes, protein denaturation, aggregation, and blood gelation. Under a heating temperature of 45° C., the normal disc-shaped erythrocytes starts to transform into the spherocytes, and substantial fragmentation of erythrocytes occurs after the heating temperature reaches 60° C. Meanwhile, the protein denaturation is a continuous process which depends on both the heating temperature and heating duration. For example, an elongated heating of 1 hour under a heating temperature of 60° C. is sufficient to convert the liquid blood into a solid gel matrix, and a rapid heating of 1 minute under a heating temperature of 85° C. can also reach the coagulation.

Thermal coagulation of blood is a result of intramolecular hydration of serum proteins, primarily in the albumin fraction. Because formation of the blood coagulum is thermally driven, the presence of chemical anticoagulants does not impair the thermal formation of the blood coagulum. See Am. J. of Medicine 1950, 745.

II. Definitions

"Blood-clot microvalve" refers to a microvalve in a capillary tube formed by a thermally induced blood clot.

"Capillary tube" refers to a tube up to several centimeters in length having a width and heighth on the scale of hundreds of microns, or smaller, for transporting fluid. The capillary tubes can be in a microfluidic device. "Segment" refers to a portion of the capillary tube, and includes adjacent and non-adjacent segmetns. A capillary tube can include any number of segments. The segments can be any suitable length and can all have the same length or different lengths.

"Blood" refers to whole blood and any combination of the constituents of blood, such as cells (erythrocytes, leukocytes, thrombocytes or platelets), red blood cells, white blood cells, plasma, serum albumin, blood-clotting factors, immunoglobulins, lipoproteins, and various other proteins and electrolytes. Blood can be from any suitable animal, such as a mammal including a human.

"Solid blood coagulum" refers to a coagulated mass formed from blood.

"Threshold differential pressure" refers to the minimum pressure differential across the solid blood coagulum.

"Anticoagulant" refers to a substance or compound that prevents coagulation, such as coagulation of blood. Suitable anticoagulants include, but are not limited to, ethylenediamine tetraacetic acid (EDTA).

"Modulating liquid flow" refers to increasing or decreasing the rate of flow of a liquid in a capillary tube.

III. Forming a Blood-Clot Microvalve

The present invention provides methods of forming a microvalve in a capillary tube of a microfluidic device using blood. Heating the blood above a certain temperature causes the blood to thermally coagulate and in certain instances, in the presence or the absence of a chemical coagulant. Thus, heating the blood in the capillary tube forms the blood-clot microvalve.

In some embodiments, the present invention provides a method of forming a blood-clot microvalve in a capillary tube or microchannel of a microfluidic device. The method includes heating blood in the capillary tube or microchannel at a temperature of from about 50° C. to about 100° C. for a sufficient period of time, such that a solid blood coagulum is formed having a threshold differential pressure of from about 0 psi to about 100 psi. Thus, the method forms the blood-clot microvalve.

Any microfluidic device is suitable in the inventive method.

The heating can be performed at any suitable temperature. For example, the temperature can be from 40° C. to 100° C., such as 40, 45, 50, 55, 60, 65, 70, 75, 80, 85, 90, 95 or 100° C. The temperature can be from 50° C. to 100° C., or 60° C. to 90° C., or 70° C. to 80° C. In some embodiments, the temperature can be from about 60° C. to about 90° C. In other embodiments, the temperature can be from about 70° C. to about 80° C. In some other embodiments, the temperature can be about 75° C.

The blood-clot microvalve formed can be stable to any suitable threshold differential pressure. For example, the threshold differential pressure can be greater than 0 psi, 5, 10, 20, 30, 40, 50 psi, or greater. The threshold differential pressure can be from about 0 psi to about 100 psi, or from about 25 psi to about 100 psi, or from about 40 psi to about 100 psi, or from about 10 psi to about 75 psi, or from about 25 psi to about 75 psi, or from about 30 psi to about 50 psi. In some embodiments, the threshold differential pressure can be from 0 psi to about 100 psi. In other embodiments, the threshold differential pressure can be from about 10 psi to about 75 psi. In some other embodiments, the threshold differential pressure can be from about 30 psi to about 50 psi. In still other embodiments, the threshold differential pressure can be about 40 psi.

The heating can be for any suitable period of time, with less time typically needed at higher temperatures to form the solid-blood coagulum having a certain threshold differential pressure. For example, the heating can be for a period of at least about 1 second, or 10, 30 or about 60 seconds. The heating can also be for a period of at least about 1 minute, or 2, 3, 4, 5, 6, 7, 8, 9 or about 10 minutes. The heating can also be for a period of from about 1 second to about 10 minutes, or about 1 minute to about 10 minutes, or about 2 minutes to about 5 minutes. The heating can also be for a period of about 1 minute, or 2, 3, 4, 5, 6, 7, 8, 9 or about 10 minutes. In some embodiments, the heating can be for a period of about 1 second to about 10 minutes. In other embodiments, the heating can be for a period of about 2 minutes to about 5 minutes. In some other embodiments, the heating can be for a period of about 3 minutes.

Any combination of temperature and time is useful for forming the blood-clot microvalves of the present invention. For example, the heating can be for a period of about 10 seconds at a temperature of about 90° C., or for a period of about 3 minutes at about 75° C. In some embodiments, the heating is at 75° C. for a period of about 3 minutes.

The blood used in the method of the present invention can be any suitable blood. The blood can be from any animal. The blood is preferably from a mammal, such as primates (e.g., humans), cows, sheep, goats, horses, dogs, cats, rabbits, rats, mice and the like. Blood can refer to whole blood or any components of blood, such as serum, plasma, red blood cells (RBCs), and white blood cells (WBCs). The blood can also include synthetic additives such as an anticoagulant or other blood stabilizer or preservative. Anticoagulants that can be present in the blood include, but are not limited to, ethylenediaminetetraacetic acid (EDTA), coumadin, warfarin, heparin, citrate, or oxalate.

In some embodiments, the blood can be human blood. In other embodiments, the blood can be plasma. In some other embodiments, the blood can include an anticoagulant. In still other embodiments, the blood can include ethylenediaminetetraacetic acid (EDTA).

The heating can be accomplished by any suitable means known in the art. For example, the heating can be accomplished by systemic heating using a water bath or other fluid bath, or heating only a portion of the capillary tubes such as with a laser or integrated ohmic heater. In some embodiments, the heating is performed using a laser.

The basic principle of the laser induce heating is that the hemoglobin in erythrocytes has good absorbance towards the light in visible wavelength range, and the absorbed energy is then converted into heat, rising the temperature of the blood sample. Therefore, when a laser of certain intensity is used, sufficient heating can be generated and leads to the thermal coagulation. In this study, a 488 nm continuous-wave laser is employed for this purpose. The laser beam is focused into a confined area, the size of which is slightly larger than the valve zone. By optimizing the intensity and duration of the laser, blood clogging can be induced inside the valve zone with minimized excessive heating.

The heating of the capillary tube can involve heating the entire capillary tube and microfluidic device, or heating one or more segments of the capillary tube. The capillary tube can include any suitable number of segments, such as 2, 3, 4, 5, 6, 7, 8, 9, 10 or more. When the capillary tube includes at least 2 segments, any number of the segments can be heated. For example, when the capillary tube includes 3 segments, 2 of the segments can be separately heated. When the capillary tube includes 5 segments, 3 of the segments can be separately heated. The heated segments can be adjacent to one another or separated by non-heated segments.

The blood-clot microvalves formed in the various segments of a single capillary tube or in different capillary tubes of a microfluidic device can have the same or different threshold differential pressures.

In some embodiments, the capillary tube includes at least two segments, such that only one segment is heated to form the blood-clot microvalve in the heated segment. In other embodiments, the capillary tube includes at least three segments, such that at least two non-adjacent segments are heated to form the blood-clot microvalve in each of the heated segments.

The capillary tube can be any suitable length and width or diameter. For example, the capillary tube can have a width of from about 1 µm and about 10,000 µm, or about 10 µm to about 1000 µm, or from about 10 µm to about 500 µm. The length of the capillary tube can be from about 100 µm to about 10 centimeters, or from about 100 µm to about 1 cm, or from 500 µm to about 5 mm.

In some embodiments, the method of the present invention includes heating human blood, wherein the human blood includes ethylenediaminetetraacetic acid (EDTA), in the capillary tube at a temperature of about 75° C. for a period of about 3 minutes, such that the solid blood coagulum formed has a threshold differential pressure of about 40 psi, thus forming the blood-clot microvalve.

IV. Modulating Liquid Flow

The present invention also provides methods of modulating blood flow in a capillary tube by forming a reversible blood-clot microvalve, and then, optionally, removing the blood-clot microvalve.

In some embodiments, the present invention provide a method of modulating liquid flow through a capillary tube or microchannel of a microfluidic device. The method includes heating blood in the capillary tube or microchannel at a temperature of from about 50° C. to about 100° C. for a sufficient period of time, such that a solid blood coagulum is formed having a threshold differential pressure of from about 0 psi to about 100 psi, thus modulating the liquid flow through the capillary tube. In other embodiments, the method includes heating human blood, wherein the human blood includes ethylenediaminetetraacetic acid (EDTA), in the capillary tube at a temperature of about 75° C. for a period of about 3 minutes, such that the solid blood coagulum is formed having a threshold differential pressure of about 40 psi.

Modulating the liquid flow also includes increasing the liquid flow in the capillary tube. This can be accomplished by removing the blood-clot microvalve formed in the methods described above. The blood-clot microvalve that is formed in the above methods is susceptible to sustained high temperatures which breakdown the bonds formed during the initial formation of the solid blood coagulum. Temperatures suitable for removal of the solid blood coagulum are from about 75° C. to about 100° C., or from about 80, 85, 90, or 95° C. to about 100° C. The temperature for removal of the solid blood coagulum can be about 85° C., or 86, 87, 88, 89, 90, 91, 92, 93, 94, 95, 96, 97, 98, 99 or about 100° C. In some embodiments, the method also includes heating the solid blood coagulum at a temperature of at least 90° C. to remove the solid blood coagulum.

EXAMPLES

Example 1

Formation of Blood-Clot Microvalve

Human whole blood from healthy donors was used. Blood samples were purchased from Hemacare Corp. (CA, USA) and tested within 48 hours after drawing. The samples, after a routine analysis with respect to the concentration of erythrocytes, hemoglobin and other standard blood parameters of interest, were kept in the standard 5 ml purple tubes with Ethylenediaminetetraacetic acid (EDTA) coating and stored in 4° C. refrigerator before experiments.

The thermal coagulation was studied using glass capillary tubes (0.38 mm diameter, 10 µL Accu-Fill Micropet). For each test, the capillary tube was loaded with 2 µL, of blood and heated in a water bath to form the clog. The temperature of the water bath was constantly monitored with a thermometer. The tube was then connected to the test configuration shown in FIG. 2 by epoxy, and the mechanical strength of the blood clog, in terms of the back pressure it could withstand, was measured. An increasing air pressure with a ramp rate of 1 psig/5 sec was applied continuously on one end of the clog. The maximum back pressure was recorded as the pressure before either the clog bursting or air leakage observed by sealing the other end of the tube with a water drop. A wide range of heating temperatures (60, 65, 70, 75, 80, 85, 90° C.) and variable heating times (0, ⅙, ½, 1, 2, 3, 5 and 10 min) were evaluated.

Additional experiments were performed with PDMS devices fabricated using a standard one-layer PDMS/glass bonding process. First, PDMS (Sylgard, 10:1 ratio of base and curing agent) was poured onto a SU8 mold to form the microfluidic channels. After partial curing in an oven at 80° C. for 30 minutes, the PDMS sheet was peeled off and cut into individual devices. The fluidic ports were made by the punching of a syringe needle. Then the PDMS block was bonded to a cleaned glass slide and further cured at 100° C. for 2 hours to form the final device.

Figure 1:
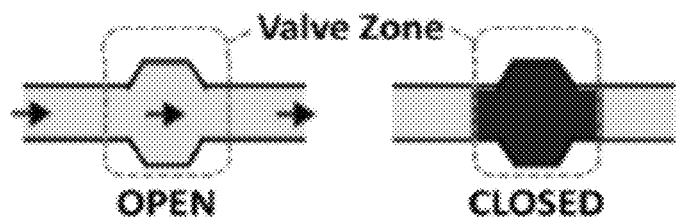
FIG. 1 shows an illustration of the operation principle of the blood clogging valve. The fluidic channel is normally open for blood to flow through. To close the valve, the blood inside the valve zone is locally heated, forming a solid clog to physical block the channel.

FIG. 1 illustrates the basic principle of utilizing this coagulation property as an open-to-close valve. The valve is normally open, allowing the blood sample to flow freely through the microfluidic channel. To actuate the valve, the valving zone is locally heated to transform the blood inside into a solidified coagulum. The blood clog hence seals the entire cross section of the fluidic channel and physically stems the flow, which realizes a one-time use open-to-close valve. The structure of this valve is simple, but extremely elegant.

For local thermal coagulation of the blood inside the valve zone, a focused laser beam is used to induce the local blood heating. Laser induced coagulation has been used in eye surgeries to finely cauterize ocular blood vessels. A similar procedure is used here to create blood clog in microfluidic channels.

Figure 2:
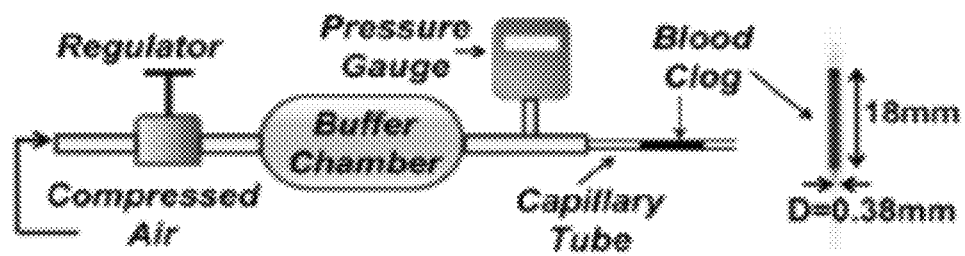
FIG. 2 shows a schematic of the back pressure measurement configuration and a picture of a capillary tube with blood clog formed inside.
Figure 3:
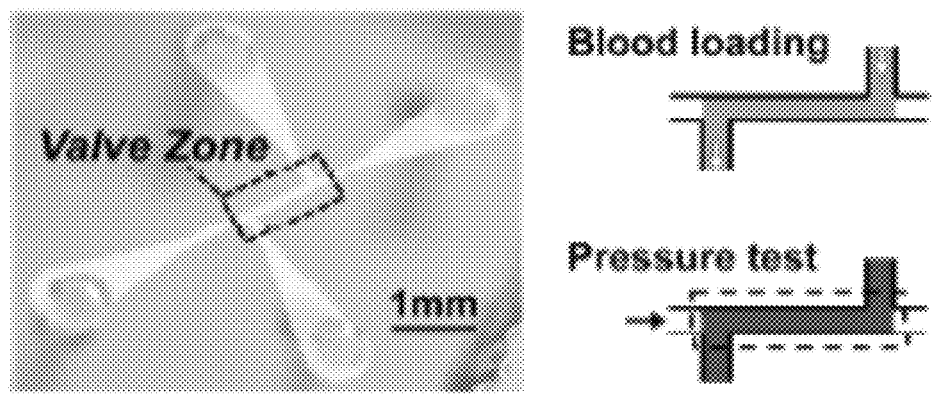
FIG. 3 shows a picture (Left) of the PDMS device for the pressure test of clogging in microfluidic channels, and an illustration (Right) of the test operation procedure. The dashed area marks the main valve zone.

FIG. 3 shows the PDMS device with the microfluidic channels for testing the back pressure that the blood clog can hold. The device consists of a main valve zone and four fluidic ports. The size of the clog is mainly decided by the dimension of the valve zone. Two fluidic ports are used for loading blood, while the other two are used to applied an elevated air pressure on the two ends of the valve zone. After filled with blood, the device was heated with the glass side contacting the heated water bath to induce the blood thermal coagulation. Metal tubes were inserted into the PDMS ports to provide world-to-chip connections for the compressed air and then the back pressure was tested by the same configuration as shown in FIG. 2.

The laser platform used in these experiments for laser induced thermal coagulation included the following: An optical microscope (Axioskop 50, Zeiss) was modified to accommodate a 20 mW, 488 nm solid-state laser by replacing the mounted camera with a optical fiber delivering the laser. The laser beam was first passed through a beam splitter (70% transmission) and then focused by a 20× objective lens into a 40 μm diameter area. The beam splitter could be adjusted between two positions. With the splitter slid in, the laser was shielded and only the bright field image was captured by the eyepiece camera. With the splitter pulled out, the laser was allowed to pass through for heating the blood sample, while both the bright field image and the image of the laser spot were captured. A 488 nm high pass filter was used to prevent most of the reflected laser from entering the camera. The device was mounted on a sample stage, which supported the z-axis focusing, and both the x-axis and y-axis tuning of the device position. The alignment between the clogging valve and the laser illumination was monitored through the live video of the camera.

Figure 4:
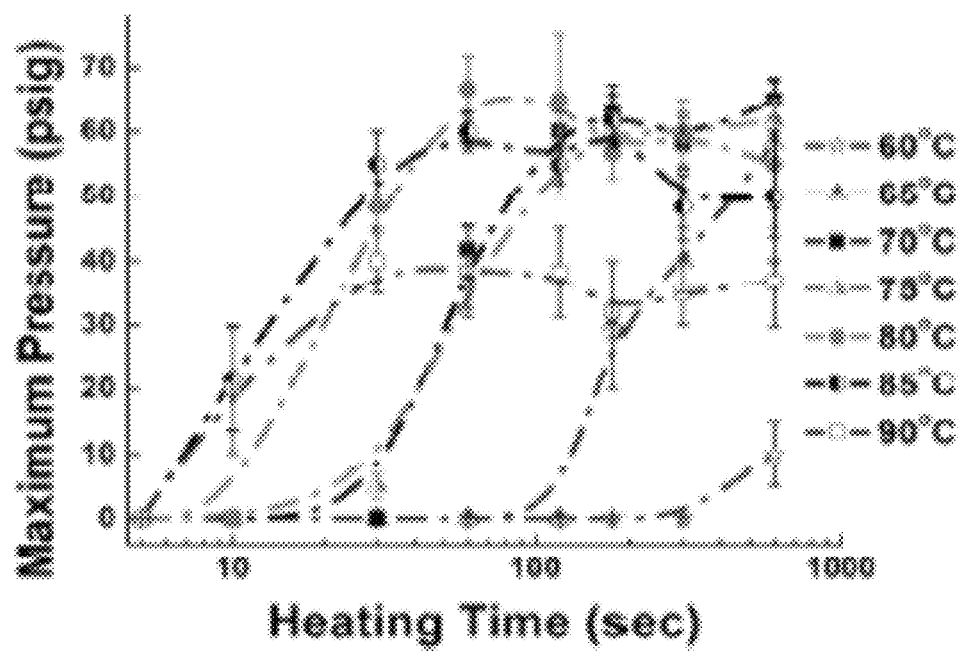
FIG. 4 shows the measured maximum back pressure of the blood clog formed in capillary tubes vs. heating time with respect to different heating temperatures.

FIG. 4 shows the results of the maximum back pressure versus heating time under different heating temperatures, which is measured from the clog in capillary tubes. For a heating temperature of 60° C., the blood remains in liquid form after a 5 min heating period. After 10 min heating, a gel-like clog was formed but could only withstand a back pressure of 10 psig. For temperatures between 65° C. and 90° C., the coagulation occurs with shorter heating times, as expected from the continuous protein denaturation process. For each temperature, the withstood back pressure first rises with increasing heating time before reaching a relatively stable range, where the clog formed at 90° C. withstands a pressure (30-40 psig) lower than the pressure (50-70 psig) of the clogs formed at temperatures between 65° C. and 85° C. This observation can be attributed to the excessive dehydration of the sample under the 90° C. heating. In general, clog formed under a 70-90° C., 1-3 min heating withstands a back pressure of 30 psig or higher.

Figure 5:
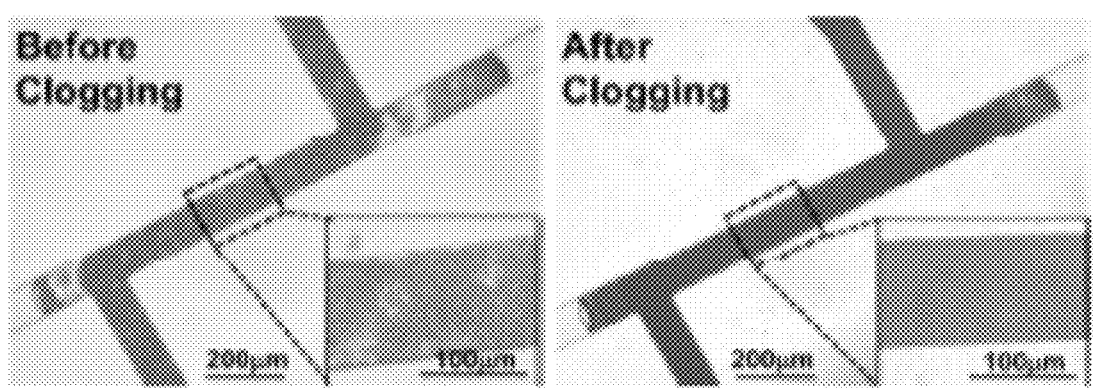
FIG. 5 shows microscopy pictures of the blood in a PDMS channel before (Left) and after (Right) clogging. The inset shows the zoom-in picture of the outlined area (100 μm channel height).

FIG. 5 shows the microscopic pictures of the blood clog formed in the PDMS channel. At beginning, the blood is in liquid form, where the individual erythrocyte cells and the surrounding plasma are clearly distinguishable. After an 80° C., 3 min heating, a uniformly distributed coagulum is formed, blocking the whole cross section of the fluidic channel. Two valve designs with same channel height and width but different channel length, are tested under this heating condition, and the results, as summarized in Table 1 (results show the mean value of three tests), show that the clogged valve withstands a back pressure of 35 psig or higher.

TABLE 1

Measured maximum back pressure of the blood clog from two geometry designs (W: width, H: height, L: length)

| Design | Dimension (μm) W × H × L | Pressure (psig) |
|---|---|---|
| A | 100 × 50 × 800 | 35 ± 8 |
| B | 101 × 50 × 1600 | >50, PDMS delaminated |

Figure 6:
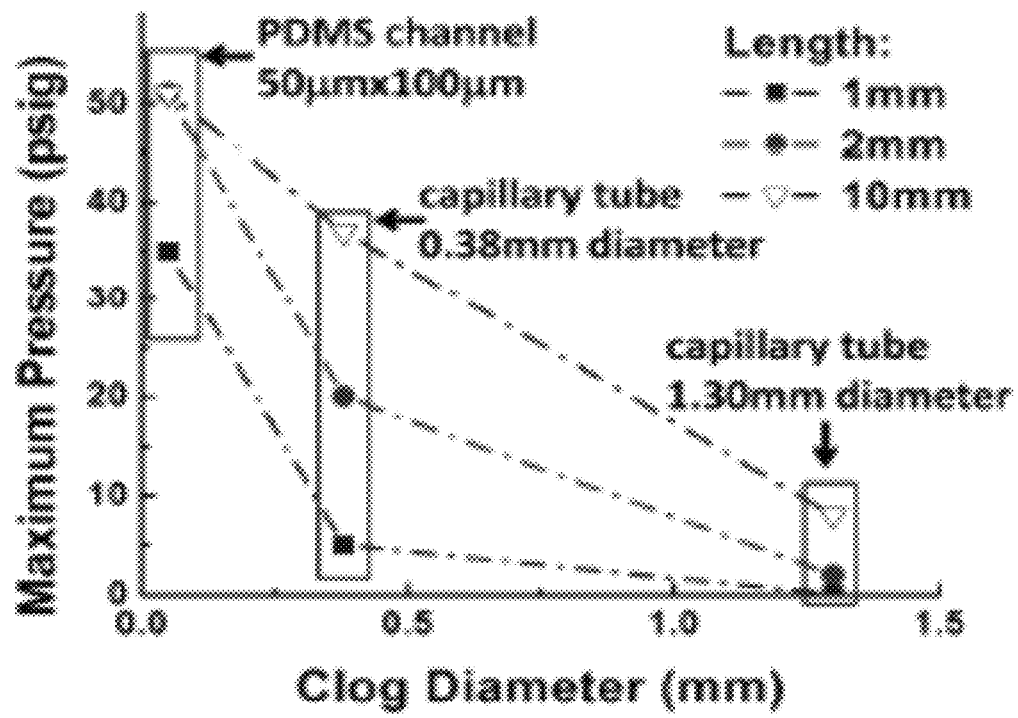
FIG. 6 shows a summary of the measured results of maximum back pressure vs.

FIG. 6 summarizes the results of valve closed ("clogged") formed in the capillary tube and in the PDMS channel, and the minimum back pressures withstood were plotted versus the clog size. It shows that clogs formed in smaller tubes/channels withstand higher minimum back pressures, which suggests the scaling advantage of this approach for microfluidics.

FIG. 7 shows the microscopic pictures of localized valving ("clogging") introduced by the laser illumination. The microfluidic channel is 30 μm high and 36 μm wide, which is pre-loaded with human whole blood. The laser spot (40 μm in diameter) was aligned along the center of the fluidic channel. After a 1 min illumination, the section of the blood underneath the laser spot was locally solidified, and seals the entire cross section of the channel. In the picture, the clog shows a darker color than the surrounding blood sample. This localized clog was tested by the same configuration as shown in FIG. 2, and it withstands a back pressure of 26±4 psig, sufficient for most low-pressure microfluidic applications.

FIG. 8 illustrates the implementation of this clogging valve in a microfluidic cytometer we developed. The sample chamber has four fluidic ports. The upper port connecting to the upstream pump and the lower port connecting to downstream analysis are initially closed, so that the blood sample can be loaded into the chamber through the two side ports. After filling up the whole chamber, both of the two loading ports are filled with blood and can be sealed by the laser-induced clogging. Then the upstream pump starts to push the sample for downstream analysis, and the delivered sample volume is controlled by the dimensions of the chamber.

A PDMS device is used to demonstrate this operation. As shown in FIG. 9, blood samples are firstly sealed inside the chamber by two clogging valves and then pushed out for downstream analysis, where a volume of 0.1 μL, blood was successfully delivered.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of forming a blood-clot microvalve in a microfluidic device comprising heating a blood or blood plasma sample in a capillary tube or microchannel of the microfluidic device at a temperature of from about 50° C. to about 100° C. for a sufficient period of time, such that a solid blood coagulum is formed in the capillary tube or microchannel having a threshold differential pressure of greater than 0 psi to about 100 psi, thus forming the blood-clot microvalve.

2. The method of claim 1, wherein the temperature is from about 60° C. to about 90° C.

3. The method of claim 1, wherein the temperature is from about 70° C. to about 80° C.

4. The method of claim 1, wherein the temperature is about 75° C.

5. The method of claim 1, wherein the solid blood coagulum has a threshold differential pressure of from about 10 psi to about 75 psi.

6. The method of claim 1, wherein the solid blood coagulum has a threshold differential pressure of from about 30 psi to about 50 psi.

7. The method of claim 1, wherein the solid blood coagulum has a threshold differential pressure of about 40 psi.

8. The method of claim 1, wherein the blood is heated for a period of about 2 to about 5 minutes.

9. The method of claim 1, wherein the blood is heated for a period of about 3 minutes.

10. The method of claim 1, wherein the blood is heated at about 75° C. for about 3 minutes.

11. The method of claim 1, wherein the blood comprises an anticoagulant.

12. The method of claim 1, wherein the blood comprises ethylenediaminetetraacetic acid (EDTA).

13. The method of claim 1, wherein the blood is human blood.

14. The method of claim 13, wherein the human blood comprises ethylenediaminetetraacetic acid (EDTA), and the capillary tube is heated at a temperature of about 75° C. for a period of about 3 minutes, such that the solid blood coagulum formed has a threshold differential pressure of about 40 psi.

15. The method of claim 1, wherein the sample is blood plasma.

16. The method of claim 1, wherein the capillary tube comprises at least two segments, such that only one segment is heated to form the blood-clot microvalve in the heated segment.

17. The method of claim 1, wherein the capillary tube comprises at least three segments, such that at least two non-adjacent segments are heated to form a blood-clot microvalve in each of the heated segments.

18. A method of modulating liquid flow through a microfluidic device comprising heating a blood or blood plasma sample in a capillary tube or microchannel of the microfluidic device at a temperature of from about 50° C. to about 100° C. for a sufficient period of time to form a solid blood coagulum, such that the solid blood coagulum forms a microvalve in the capillary tube or microchannel having a threshold differential pressure of greater than 0 psi to about 100 psi, thus modulating the liquid flow through the microfluidic device.

19. The method of claim 18, wherein the blood is human blood and comprises ethylenediaminetetraacetic acid (EDTA), and the capillary tube is heated at a temperature of about 75° C. for a period of about 3 minutes, such that the solid blood coagulum is formed having a threshold differential pressure of about 40 psi.

20. The method of claim 19, further comprising heating the solid blood coagulum at a temperature of at least 90° C. to remove the solid blood coagulum.

* * * * *